US009589574B1

(12) United States Patent
Klimanis et al.

(10) Patent No.: US 9,589,574 B1
(45) Date of Patent: Mar. 7, 2017

(54) ANNOYANCE NOISE SUPPRESSION

(71) Applicant: Doppler Labs, Inc., New York, NY (US)

(72) Inventors: Gints Klimanis, SunnyVale, CA (US); Anthony Parks, Queens, NY (US)

(73) Assignee: Doppler Labs, Inc., San Francisco, CA (US)

( * ) Notice: Subject to any disclaimer, the term of this patent is extended or adjusted under 35 U.S.C. 154(b) by 0 days.

(21) Appl. No.: 14/941,458

(22) Filed: Nov. 13, 2015

(51) Int. Cl.
*A61F 11/06* (2006.01)
*G10L 21/0232* (2013.01)
(Continued)

(52) U.S. Cl.
CPC .......... *G10L 21/0232* (2013.01); *G10L 25/84* (2013.01); *G10L 25/90* (2013.01);
(Continued)

(58) Field of Classification Search
CPC .......... H04R 1/00; H04R 1/1083; H04R 1/08; H04R 1/1091; H04R 2410/01; H04R 2410/05; H04R 2499/13; H04R 5/02; H04R 29/00; G10K 11/178; G10K 11/1784; G10K 11/1786; G10K 11/1788; G10K 15/04; G10K 2210/1282; G10K 2210/228; G10K 2210/3032; G10K 2210/3033; G10K 2210/3056; G10K 11/16; G10H 1/0041; H03G 3/001; H03G 3/20; H03G 3/32; H03G 7/002; G10L 21/02; G10L 11/04; G10L 19/14; G10L 15/20; H04B 15/00; H04B 1/00; H03B 29/00
USPC ...... 381/72, 72.1, 74, 77–79, 85, 86, 91–93, 381/94.1–94.5, 94.7, 94.8, 95, 97–115, 381/118–123, 316–318, 320, 321, 71.1, 381/71.3, 71.4, 71.6, 71.8, 71.11–71.14, 381/56, 57; 700/94; 704/275, E15.039,
(Continued)

(56) References Cited

U.S. PATENT DOCUMENTS 4,736,432 A 4/1988 Cantrell
4,878,188 A 10/1989 Ziegler, Jr.
(Continued)

OTHER PUBLICATIONS

Rani et al., "A Review of Diverse Pitch & Detection Methods", journal, International Journal of Science and Research (IJSR), ISSN (Online): 2319-7064, Index Copernicus Value (2013): 6.14 | Impact Factor (2013): 4.438, vol. 4 Issue 3, Mar. 2015, 4 total pages.
(Continued)

*Primary Examiner* — Leshui Zhang
(74) *Attorney, Agent, or Firm* — Van Pelt, Yi and James LLP

(57) ABSTRACT

Personal audio systems and methods are disclosed. A personal audio system includes a voice activity detector to determine whether or not an ambient audio stream contains voice activity, a pitch estimator to determine a frequency of a fundamental component of an annoyance noise contained in the ambient audio stream, and a filter bank to attenuate the fundamental component and at least one harmonic component of the annoyance noise to generate a personal audio stream. The filter bank implements a first filter function when the ambient audio stream does not contain voice activity, or a second filter function when the ambient audio stream contains voice activity.

28 Claims, 7 Drawing Sheets

© 2015 Doppler Labs

(51) Int. Cl.
*G10L 25/84* (2013.01)
*G10L 25/90* (2013.01)
*H04R 29/00* (2006.01)
*G10L 21/0216* (2013.01)

(52) U.S. Cl.
CPC .. *H04R 29/004* (2013.01); *G10L 2021/02163* (2013.01); *H04R 2460/01* (2013.01)

(58) Field of Classification Search
USPC .......... 704/E15.045, 226, E19.013, E19.014, 704/E21.014; 455/501, 63.1, 67.13, 455/569.1, 569.2, 570, 114.2, 135, 222, 455/283, 296, 297, 308, 309, FOR. 228; 379/392.01
See application file for complete search history.

(56) References Cited

U.S. PATENT DOCUMENTS 5,251,263 A 10/1993 Andrea et al.
5,657,422 A * 8/1997 Janiszewski .......... G10L 19/012 704/229
5,745,581 A 4/1998 Eatwell et al.
6,523,003 B1 * 2/2003 Chandran ........... G10L 21/0208 704/225
7,289,626 B2 10/2007 Carter et al.
8,194,873 B2 6/2012 Pan et al.
8,204,242 B2 6/2012 Pan et al.
8,335,318 B2 12/2012 Pan
8,423,357 B2 4/2013 Kulakcherla et al.
8,600,743 B2 12/2013 Lindahl et al.
9,031,248 B2 5/2015 Hera
9,118,987 B2 8/2015 Pan et al.
2003/0061251 A1 3/2003 White
2006/0204025 A1 * 9/2006 Paludan-Muller ...... G10L 25/00 381/317
2007/0055508 A1 * 3/2007 Zhao ................... G10L 21/0216 704/226
2008/0240458 A1 10/2008 Goldstein et al.
2009/0254340 A1 10/2009 Sun et al.
2010/0040249 A1 2/2010 Lenhardt
2011/0166856 A1 * 7/2011 Lindahl ................... G10L 15/20 704/233
2012/0010881 A1 1/2012 Avendano et al.
2012/0189140 A1 7/2012 Hughes
2013/0058489 A1 * 3/2013 Tanaka ................. H04B 15/005 381/56
2015/0162021 A1 6/2015 Anhari et al.

OTHER PUBLICATIONS

Wang et al., "A generalized design framework for IIR digital multiple notch filters", Wang and Kundur EURASIP Journal on Advances in Signal Processing (2015) 2015:26, Mar. 20, 2015, 13 total pages.

H. Farsi et al., "Improving Voice Activity Detection Used in ITU-T G.729.B", Proceedings of the 3rd WSEAS Int. Conf. on Circuits, Systems, Signal and Telecommunications (CISST'09), ISBN: 978-960-474-42-0, Jan. 10, 2009, 5 total pages.

* cited by examiner

© 2015 Doppler Labs

© 2015 Doppler Labs

© 2015 Doppler Labs

© 2015 Doppler Labs

© 2015 Doppler Labs

© 2015 Doppler Labs

ANNOYANCE NOISE SUPPRESSION

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

RELATED APPLICATION INFORMATION

This patent is related to patent application Ser. No. 14/681,843, entitled "Active Acoustic Filter with Location-Based Filter Characteristics," filed Apr. 8, 2015; and patent application Ser. No. 14/819,298, entitled "Active Acoustic Filter with Automatic Selection Of Filter Parameters Based on Ambient Sound," filed Aug. 5, 2015, 2015.

BACKGROUND

Field

This disclosure relates generally to digital active audio filters for use in a listener's ear to modify ambient sound to suit the listening preferences of the listener. In particular, this disclosure relates to active audio filters that suppress annoyance noised based, in part, on user identification of the type of annoyance noise.

Description of the Related Art

Humans' perception to sound varies with both frequency and sound pressure level (SPL). For example, humans do not perceive low and high frequency sounds as well as they perceive midrange frequencies sounds (e.g., 500 Hz to 6,000 Hz). Further, human hearing is more responsive to sound at high frequencies compared to low frequencies.

There are many situations where a listener may desire attenuation of ambient sound at certain frequencies, while allowing ambient sound at other frequencies to reach their ears. For example, at a concert, concert goers might want to enjoy the music, but also be protected from high levels of mid-range sound frequencies that cause damage to a person's hearing. On an airplane, passengers might wish to block out the roar of the engine, but not conversation. At a sports event, fans might desire to hear the action of the game, but receive protection from the roar of the crowd. At a construction site, a worker may need to hear nearby sounds and voices for safety and to enable the construction to continue, but may wish to protect his or her ears from sudden, loud noises of crashes or large moving equipment. These are just a few common examples where people wish to hear some, but not all, of the sound frequencies in their environment.

In addition to receiving protection from unpleasant or dangerously loud sound levels, listeners may wish to augment the ambient sound by amplification of certain frequencies, combining ambient sound with a secondary audio feed, equalization (modifying ambient sound by adjusting the relative loudness of various frequencies), white noise reduction, echo cancellation, and addition of echo or reverberation. For example, at a concert, audience members may wish to attenuate certain frequencies of the music, but amplify other frequencies (e.g., the bass). People listening to music at home may wish to have a more "concert-like" experience by adding reverberation to the ambient sound. At a sports event, fans may wish to attenuate ambient crowd noise, but also receive an audio feed of a sportscaster reporting on the event. Similarly, people at a mall may wish to attenuate the ambient noise, yet receive an audio feed of advertisements targeted to their location. These are just a few examples of peoples' audio enhancement preferences.

Further, a user may wish to engage in conversation and other activities without being interrupt or impaired by annoyance noises. Examples of annoyance noises include the sounds of engines or motors, crying babies, and sirens. Commonly, annoyances noises are composed of a fundamental frequency component and harmonic components at multiples or harmonics of the fundamental frequency. The fundamental frequency may vary randomly or periodically, and the harmonic components may extend into the frequency range (e.g. 2000 Hz to 5000 Hz) where the human ear is most sensitive.

Throughout this description, elements appearing in figures are assigned three-digit reference designators, where the most significant digit is the figure number where the element is introduced and the two least significant digits are specific to the element. An element not described in conjunction with a figure has the same characteristics and function as a previously-described element having the same reference designator.

DETAILED DESCRIPTION

Description of Apparatus

Figure 1:
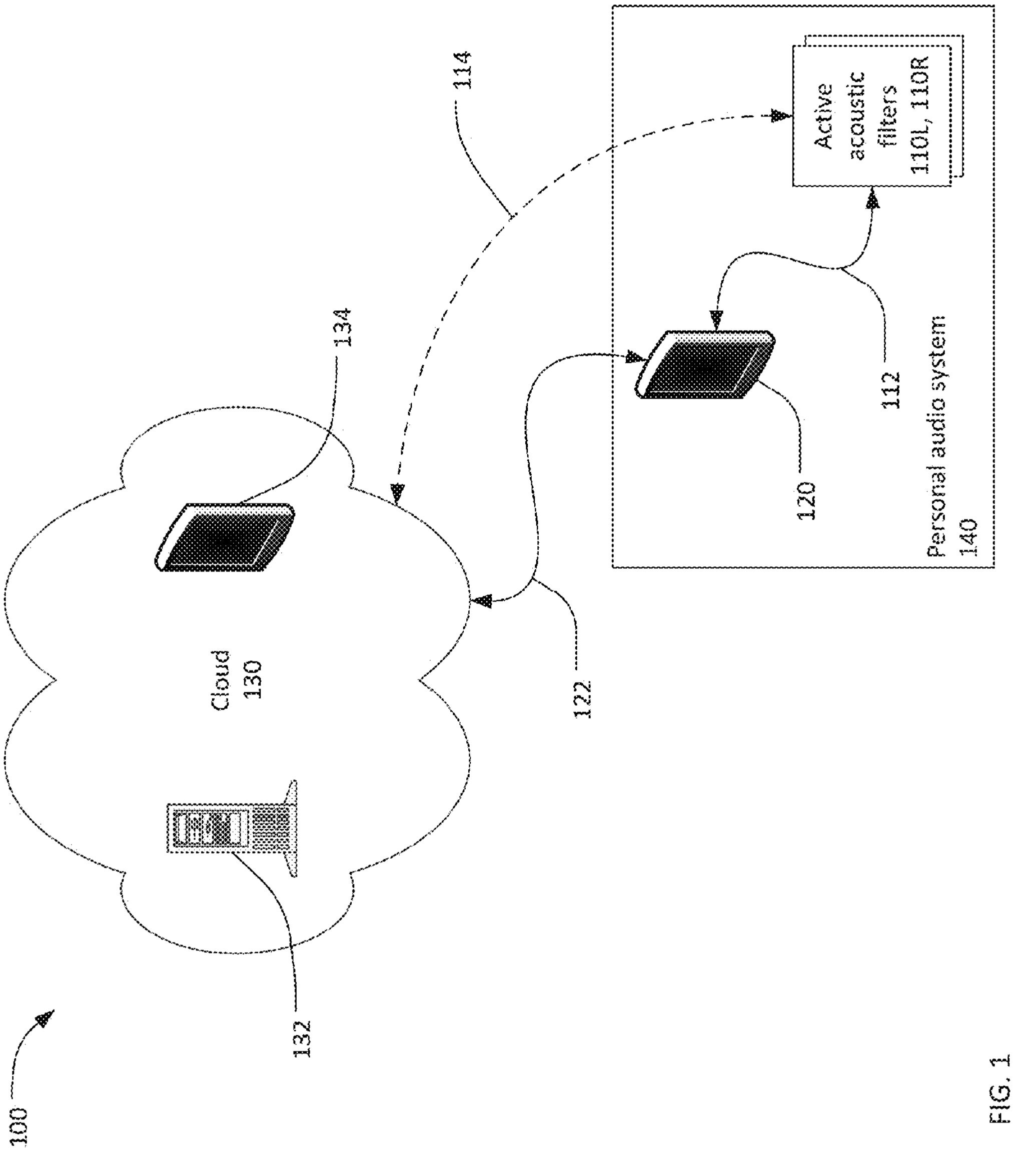
FIG. 1 is a block diagram of an environment.

Referring now to FIG. 1, an environment 100 may include a cloud 130 and a personal audio system 140. In this context, the term "cloud" means a network and all devices that may be accessed by the personal audio system 140 via the network. The cloud 130 may be a local area network, wide area network, a virtual network, or some other form of network together with all devices connected to the network. The cloud 130 may be or include the Internet. The devices within the cloud 130 may include, for example, one or more servers 134.

The personal audio system 140 includes left and right active acoustic filters 110L, 110R and a personal computing device 120. While the personal computing device 120 is shown in FIG. 1 as a smart phone, the personal computing device 120 may be a smart phone, a desktop computer, a mobile computer, a tablet computer, or any other computing device that is capable of performing the processes described herein. The personal computing device 120 may include one or more processors and memory configured to execute stored software instructions to perform the processes described herein. For example, the personal computing device 120 may run an application program or "app" to perform the functions described herein. The personal computing device 120 may include a user interface comprising a display and at least one input device such as a touch screen, microphone, keyboard, and/or mouse. The personal computing device 120 may be configured to perform geo-location, which is to say to determine its own location. Geo-location may be performed, for example, using a Global Positioning System (GPS) receiver or by some other method.

The active acoustic filters 110L, 110R may communicate with the personal computing device 120 via a first wireless communications link 112. The first wireless communications link 112 may use a limited-range wireless communications protocol such as Bluetooth®, WiFi®, ZigBee®, or some other wireless Personal Area Network (PAN) protocol. The personal computing device 120 may communicate with the cloud 130 via a second communications link 122. The second communications link 122 may be a wired connection or may be a wireless communications link using, for example, the WiFi® wireless communications protocol, a mobile telephone data protocol, or another wireless communications protocol.

Optionally, the acoustic filters 110L, 110R may communicate directly with the cloud 130 via a third wireless communications link 114. The third wireless communications link 114 may be an alternative to, or in addition to, the first wireless communications link 112. The third wireless connection 114 may use, for example, the WiFi® wireless communications protocol, or another wireless communications protocol. The acoustic filters 110L, 110R may communicate with each other via a fourth wireless communications link (not shown).

Figure 2:
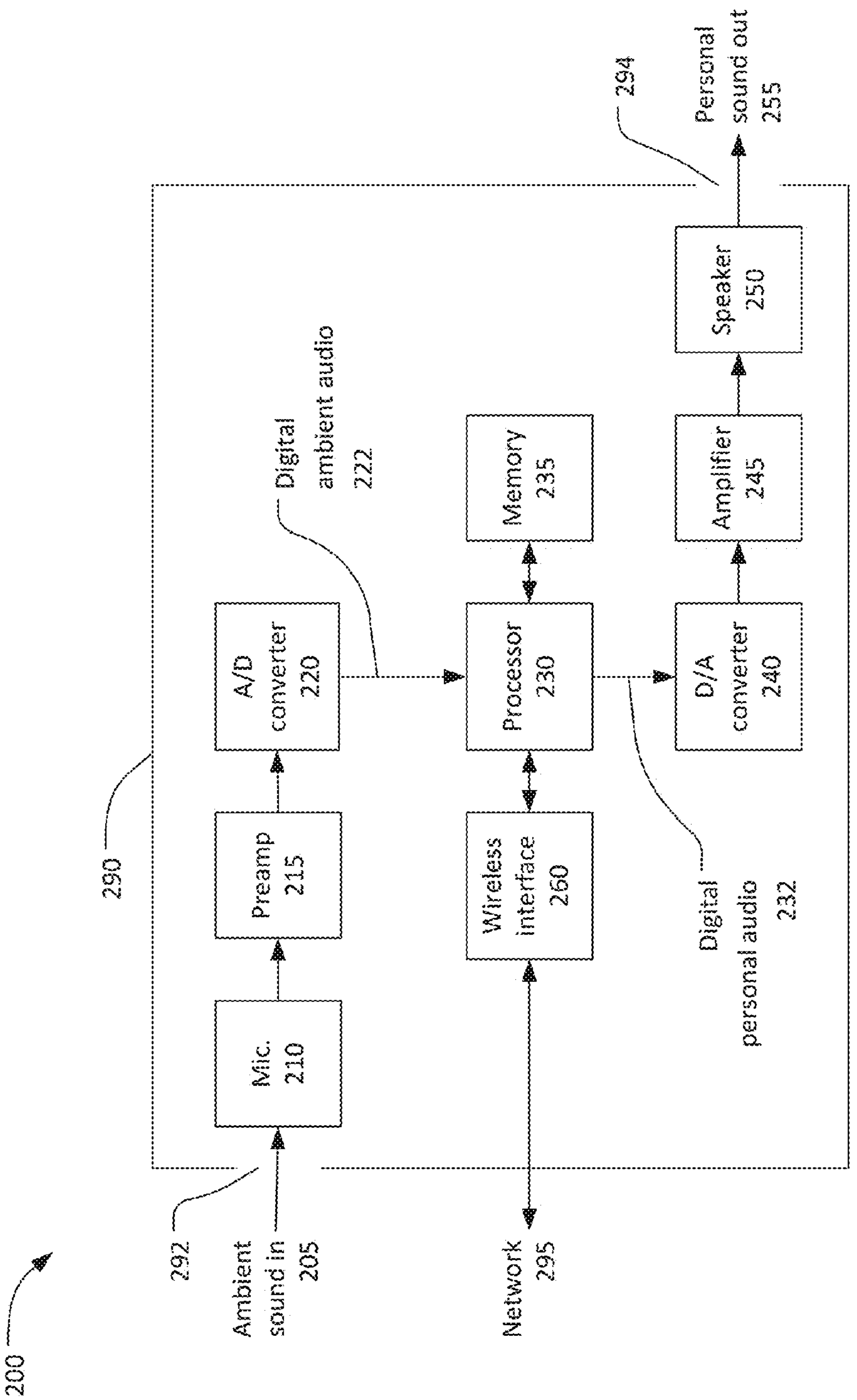
FIG. 2 is block diagram of an active acoustic filter.

FIG. 2 is block diagram of an active acoustic filter 200, which may be the active acoustic filter 110L and/or the active acoustic filter 110R. The active acoustic filter 200 may include a microphone 210, a preamplifier 215, an analog-to-digital (A/D) converter 220, a processor 230, a memory 235, an analog signal by digital-to-analog (D/A) converter 240, and amplifier 245, a speaker 250, a wireless interface 260, and a battery (not shown), all of which may be contained within a housing 290. The housing 290 may be configured to interface with a user's ear by fitting in, on, or over the user's ear such that ambient sound is mostly excluded from reaching the user's ear canal and processed personal sound generated by the active acoustic filter is provided directly into the user's ear canal. In this context, the term "sound" refers to acoustic waves propagating in air. "Personal sound" means sound that has been processed, modified, or tailored in accordance with a user's person preferences. The term "audio" refers to an electronic representation of sound, which may be an analog signal or a digital data. The housing 290 may have a first aperture 292 for accepting ambient sound and a second aperture 294 to allow the processed personal sound to be output into the user's outer ear canal.

The housing 290 may be, for example, an earbud housing. The term "earbud" means an apparatus configured to fit, at least partially, within and be supported by a user's ear. An earbud housing typically has a portion that fits within or against the user's outer ear canal. An earbud housing may have other portions that fit within the concha or pinna of the user's ear.

The microphone 210 converts ambient sound 205 into an electrical signal that is amplified by preamplifier 215 and converted into digital ambient audio 222 by A/D converter 220. The digital ambient audio 222 may be processed by processor 230 to provide digital personal audio 232. The processing performed by the processor 230 will be discussed in more detail subsequently. The digital personal audio 232 is converted into an analog signal by D/A converter 240. The analog signal output from D/A converter 240 is amplified by amplifier 245 and converted into personal sound 255 by speaker 250.

The depiction in FIG. 2 of the active acoustic filter 200 as a set of functional blocks or elements does not imply any corresponding physical separation or demarcation. All or portions of one or more functional elements may be located within a common circuit device or module. Any of the functional elements may be divided between two or more circuit devices or modules. For example, all or portions of the analog-to-digital (A/D) converter 220, the processor 230, the memory 235, the analog signal by digital-to-analog (D/A) converter 240, the amplifier 245, and the wireless interface 260 may be contained within a common signal processor circuit device.

The microphone 210 may be one or more transducers for converting sound into an electrical signal that is sufficiently compact for use within the housing 290.

The preamplifier 215 may be configured to amplify the electrical signal output from the microphone 210 to a level compatible with the input of the A/D converter 220. The preamplifier 215 may be integrated into the A/D converter 220, which, in turn, may be integrated with the processor 230. In the situation where the active acoustic filter 200 contains more than one microphone, a separate preamplifier may be provided for each microphone.

The A/D converter 220 may digitize the output from preamplifier 215, which is to say convert the output from preamplifier 215 into a series of digital ambient audio samples at a rate at least twice the highest frequency present in the ambient sound. For example, the A/D converter may output digital ambient audio 222 in the form of sequential audio samples at rate of 40 kHz or higher. The resolution of the digitized ambient audio 222 (i.e. the number of bits in each audio sample) may be sufficient to minimize or avoid audible sampling noise in the processed output sound 255. For example, the A/D converter 220 may output digital ambient audio 222 having 12 bits, 14, bits, or even higher resolution. In the situation where the active acoustic filter 200 contains more than one microphone with respective preamplifiers, the outputs from the preamplifiers may be digitized separately, or the outputs of some or all of the preamplifiers may be combined prior to digitization.

The processor 230 may include one or more processor devices such as a microcontroller, a microprocessor, and/or a digital signal processor. The processor 230 can include and/or be coupled to the memory 235. The memory 235 may store software programs, which may include an operating system, for execution by the processor 230. The memory 235 may also store data for use by the processor 230. The data stored in the memory 235 may include, for example, digital sound samples and intermediate results of processes performed on the digital ambient audio 222. The data stored in the memory 235 may also include a user's listening preferences, and/or rules and parameters for applying particular processes to convert the digital ambient audio 222 into the digital personal audio 232. The memory 235 may include a combination of read-only memory, flash memory, and static or dynamic random access memory.

The D/A converter 240 may convert the digital personal audio 232 from the processor 230 into an analog signal. The processor 230 may output the digital personal audio 232 as a series of samples typically, but not necessarily, at the same rate as the digital ambient audio 222 is generated by the A/D converter 220. The analog signal output from the D/A converter 240 may be amplified by the amplifier 245 and converted into personal sound 255 by the speaker 250. The amplifier 245 may be integrated into the D/A converter 240, which, in turn, may be integrated with the processor 230. The speaker 250 can be any transducer for converting an electrical signal into sound that is suitably sized for use within the housing 290.

The wireless interface 260 may provide digital acoustic filter 200 with a connection to one or more wireless networks 295 using a limited-range wireless communications protocol such as Bluetooth®, WiFi®, ZigBee®, or other wireless personal area network protocol. The wireless interface 260 may be used to receive data such as parameters for use by the processor 230 in processing the digital ambient audio 222 to produce the digital personal audio 232. The wireless interface 260 may be used to receive a secondary audio feed. The wireless interface 260 may be used to export the digital personal audio 232, which is to say transmit the digital personal audio 232 to a device external to the active acoustic filter 200. The external device may then, for example, store and/or publish the digitized processed sound, for example via social media.

The battery (not shown) may provide power to various elements of the active acoustic filter 200. The battery may be, for example, a zinc-air battery, a lithium ion battery, a lithium polymer battery, a nickel cadmium battery, or a battery using some other technology.

Figure 3:
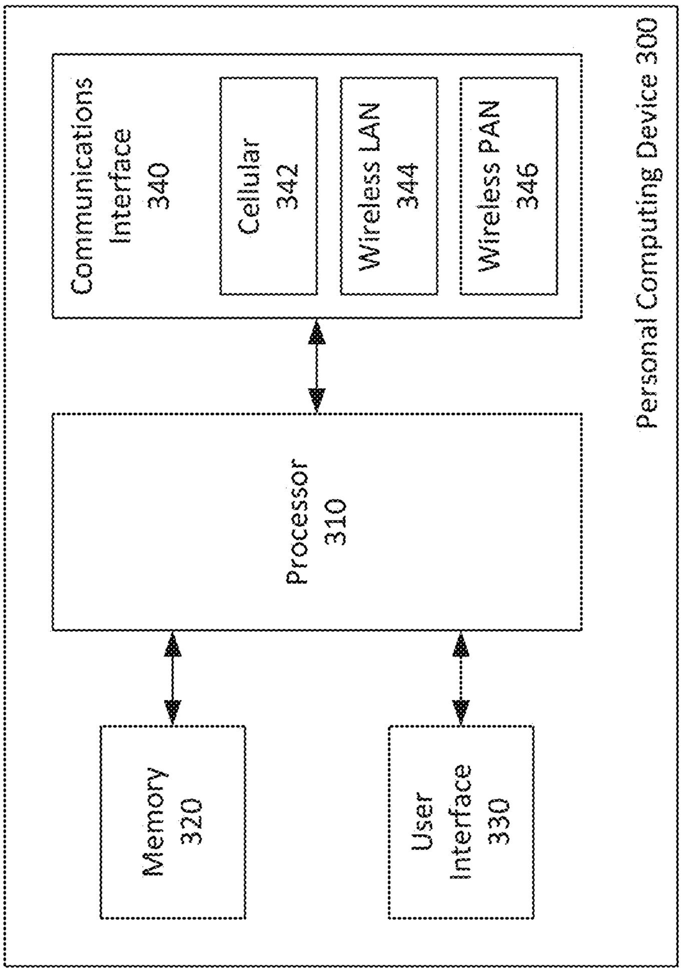
FIG. 3 is a block diagram of a personal computing device.

FIG. 3 is a block diagram of an exemplary personal computing device 300, which may be the personal computing device 120. As shown in FIG. 3, the personal computing device 300 includes a processor 310, memory 320, a user interface 330, and a communications interface 340. Some of these elements may or may not be present, depending on the implementation. Further, although these elements are shown independently of one another, each may, in some cases, be integrated into another.

The processor 310 may be or include one or more microprocessors, microcontrollers, digital signal processors, application specific integrated circuits (ASICs), or a system-on-a-chip (SOCs). The memory 320 may include a combination of volatile and/or non-volatile memory including read-only memory (ROM), static, dynamic, and/or magnetoresistive random access memory (SRAM, DRM, MRAM, respectively), and nonvolatile writable memory such as flash memory.

The communications interface 340 includes at least one interface for wireless communications with external devices. The communications interface 340 may include one or more of a cellular telephone network interface 342, a wireless Local Area Network (LAN) interface 344, and/or a wireless personal area network (PAN) interface 336. The cellular telephone network interface 342 may use one or more of the known 2G, 3G, and 4G cellular data protocols. The wireless LAN interface 344 may use the WiFi® wireless communications protocol or another wireless local area network protocol. The wireless PAN interface 346 may use a limited-range wireless communications protocol such as Bluetooth®, Wi-Fi®, ZigBee®, or some other public or proprietary wireless personal area network protocol. When the personal computing device is deployed as part of an personal audio system, such as the personal audio system 140, the wireless PAN interface 346 may be used to communicate with the active acoustic filter devices 110L, 110R. The cellular telephone network interface 342 and/or the wireless LAN interface 344 may be used to communicate with the cloud 130.

The communications interface 340 may include radio-frequency circuits, analog circuits, digital circuits, one or more antennas, and other hardware, firmware, and software necessary for communicating with external devices. The communications interface 340 may include one or more processors to perform functions such as coding/decoding, compression/decompression, and encryption/decryption as necessary for communicating with external devices using selected communications protocols. The communications interface 340 may rely on the processor 310 to perform some or all of these function in whole or in part.

The memory 320 may store software programs and routines for execution by the processor. These stored software programs may include an operating system such as the Apple® or Android® operating systems. The operating system may include functions to support the communications interface 340, such as protocol stacks, coding/decoding, compression/decompression, and encryption/decryption. The stored software programs may include an application or "app" to cause the personal computing device to perform portions of the processes and functions described herein.

The user interface 330 may include a display and one or more input devices including a touch screen.

Figure 4:
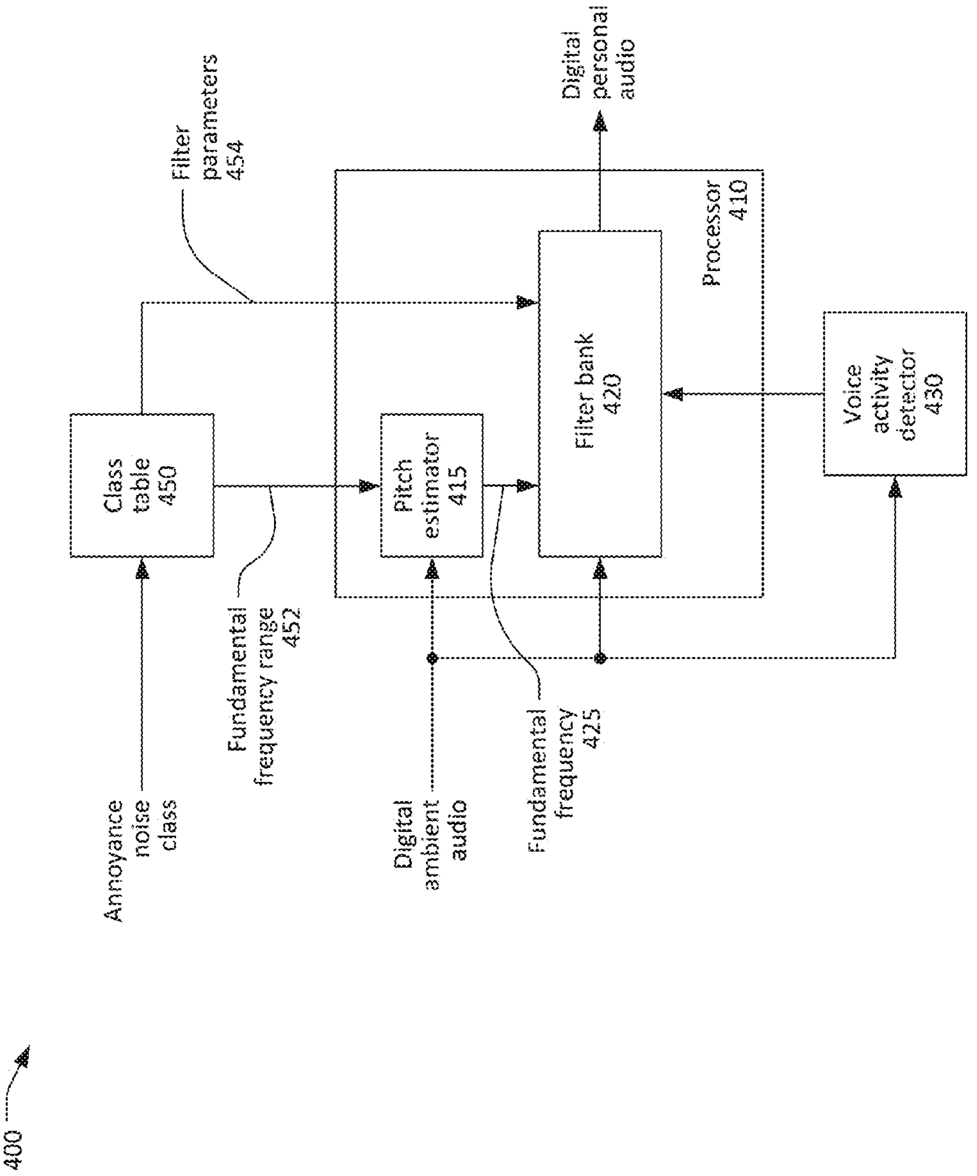
FIG. 4 is a functional block diagram of a portion of a personal audio system.

FIG. 4 shows a functional block diagram of a portion of an exemplary personal audio system 400, which may be the personal audio system 140. The personal audio system 400 may include one or two active acoustic filters, such as the active acoustic filters 110L, 110R, and a personal computing device, such as the personal computing device 120. The functional blocks shown in FIG. 4 may be implemented in hardware, by software running on one or more processors, or by a combination of hardware and software. The functional blocks shown in FIG. 4 may be implemented within the personal computing device or within one or both active acoustic filters, or may be distributed between the personal computing device and the active acoustic filters.

Techniques for improving a user's ability to hear conversation and other desirable sounds in the presence of an annoyance noise fall generally into two categories. First, the frequencies of the fundamental and harmonic components of the desirable sounds may be identified and accentuated using a set of narrow band-pass filters designed to pass those frequencies while rejecting other frequencies. However, the fundamental frequency of a typical human voice is highly modulated, which is to say changes in frequency rapidly during speech. Substantial computational and memory resources are necessary to track and band-pass filter speech. Alternatively, the frequencies of the fundamental and harmonic components of the annoyance noise may be identified and suppressed using a set of narrow band-reject filters designed to attenuate those frequencies while passing other frequencies (presumably including the frequencies of the desirable sounds). Since the fundamental frequency of many annoyance noises (e.g. sirens and machinery sounds) may vary slowly and/or predictably, the computational resources required to track and filter an annoyance noise may be lower than the resources needed to track and filter speech.

The personal audio system 400 includes a processor 410 that receives a digital ambient audio stream, such as the digital ambient audio 222. In this context, the term "stream" means a sequence of digital samples. The "ambient audio stream" is a sequence of digital samples representing the ambient sound received by the personal audio system 400.

The processor 410 includes a filter bank 420 including two or more band reject filters to attenuate or suppress a fundamental frequency component and at least one harmonic component of the fundamental frequency of an annoyance noise included in the digital ambient audio stream. Typically, the filter bank 420 may suppress the fundamental component and multiple harmonic components of the annoyance noise. The processor 410 outputs a digital personal audio stream, which may be the digital personal audio 232, in which the fundamental component and at least some harmonic components of the annoyance noise are suppressed compared with the ambient audio stream. Components of the digital ambient audio at frequencies other than the fundamental and harmonic frequencies of the annoyance noise may be incorporated into the digital personal audio stream with little or no attenuation.

The processor 410 may be or include one or more microprocessors, microcontrollers, digital signal processors, application specific integrated circuits (ASICs), or a system-on-a-chip (SOCs). The processor 410 may be located within an active acoustic filter, within the personal computing device, or may be distributed between a personal computing device and one or two active acoustic filters.

The processor 410 includes a pitch estimator 415 to identify and track the fundamental frequency of the annoyance noise included in the digital ambient audio stream. Pitch detection or estimation may be performed by time-domain analysis of the digital ambient audio, by frequency-domain analysis of the digital ambient audio, or by a combination of time-domain and frequency-domain techniques. Known pitch detection techniques range from simply measuring the period between zero-crossings of the digital ambient audio in the time domain, to complex frequency-domain analysis such as harmonic product spectrum or cepstral analysis. Brief summaries of known pitch detection methods are provided by Rani and Jain in "A Review of Diverse Pitch Detection Methods," International Journal of Science and Research, Vol. 4 No. 3, March 2015. One or more known or future pitch detection technique may be used in the pitch estimator 415 to estimate and track the fundamental frequency of the digital ambient audio stream.

The pitch estimator 415 may output a fundamental frequency value 425 to the filter bank 420. The filter bank 420 may use the fundamental frequency value 425 to "tune" its band reject filters to attenuate or suppress the fundamental component and the at least one harmonic component of the annoyance noise. A band reject filter is considered tuned to a particular frequency of the rejection band of the filter is center on, or nearly centered on the particular frequency. Techniques for implementing and tuning digital narrow band reject filters or notch filters are known in the art of signal processing. For example, an overview of narrow band reject filter design and an extensive list of references are provided by Wang and Kundur in "A generalized design framework for IIR digital multiple notch filters," EURASIP Journal on Advances in Signal Processing, 2015:26, 2015.

The fundamental frequency of many common annoyance noise sources, such as sirens and some machinery noises, is higher than the fundamental frequencies of human speech. For example, the fundamental frequency of human speech typically falls between 85 Hz and 300 Hz. The fundamental frequency of some women's and children's voices may be up to 500 Hz. In comparison, the fundamental frequency of emergency sirens typically falls between 450 Hz and 800 Hz. Of course, the human voice contains harmonic components which give each person's voice a particular timbre or tonal quality. These harmonic components are important both for recognition of a particular speaker's voice and for speech comprehension. Since the harmonic components within a particular voice may overlap the fundamental component and lower-order harmonic components of an annoyance noise, it may not be practical or even possible to substantially suppress an annoyance noise without degrading speaker and/or speech recognition.

The personal audio system 400 may include a voice activity detector 430 to determine if the digital ambient audio stream contains speech in addition to an annoyance noise. Voice activity detection is an integral part of many voice-activated systems and applications. Numerous voice activity detection methods are known, which differ in latency, accuracy, and computational resource requirements. For example, a particular voice activity detection method and references to other known voice activity detection techniques is provided by Faris, Mozaffarian, and Rahmani in "Improving Voice Activity Detection Used in ITU-T G.729.B," Proceedings of the 3$^{rd}$ WSEAS Conference on Circuits, Systems, Signals, and Telecommunications, 2009. The voice activity detector 430 may use one of the known voice activity detection techniques, a future developed activity detection technique, or a proprietary technique optimized to detection voice activity in the presence of annoyance noises.

When voice activity is not detected, the processor 410 may implement a first bank of band-reject filters 420 intended to substantially suppress the fundamental component and/or harmonic components of an annoyance noise. When voice activity is detected (i.e. when both an annoyance noise and speech are present in the digital ambient audio), the tracking noise suppression filter 410 may implement a second bank of band-reject filters 420 that is a compromise between annoyance noise suppression and speaker/speech recognition.

Figure 5:
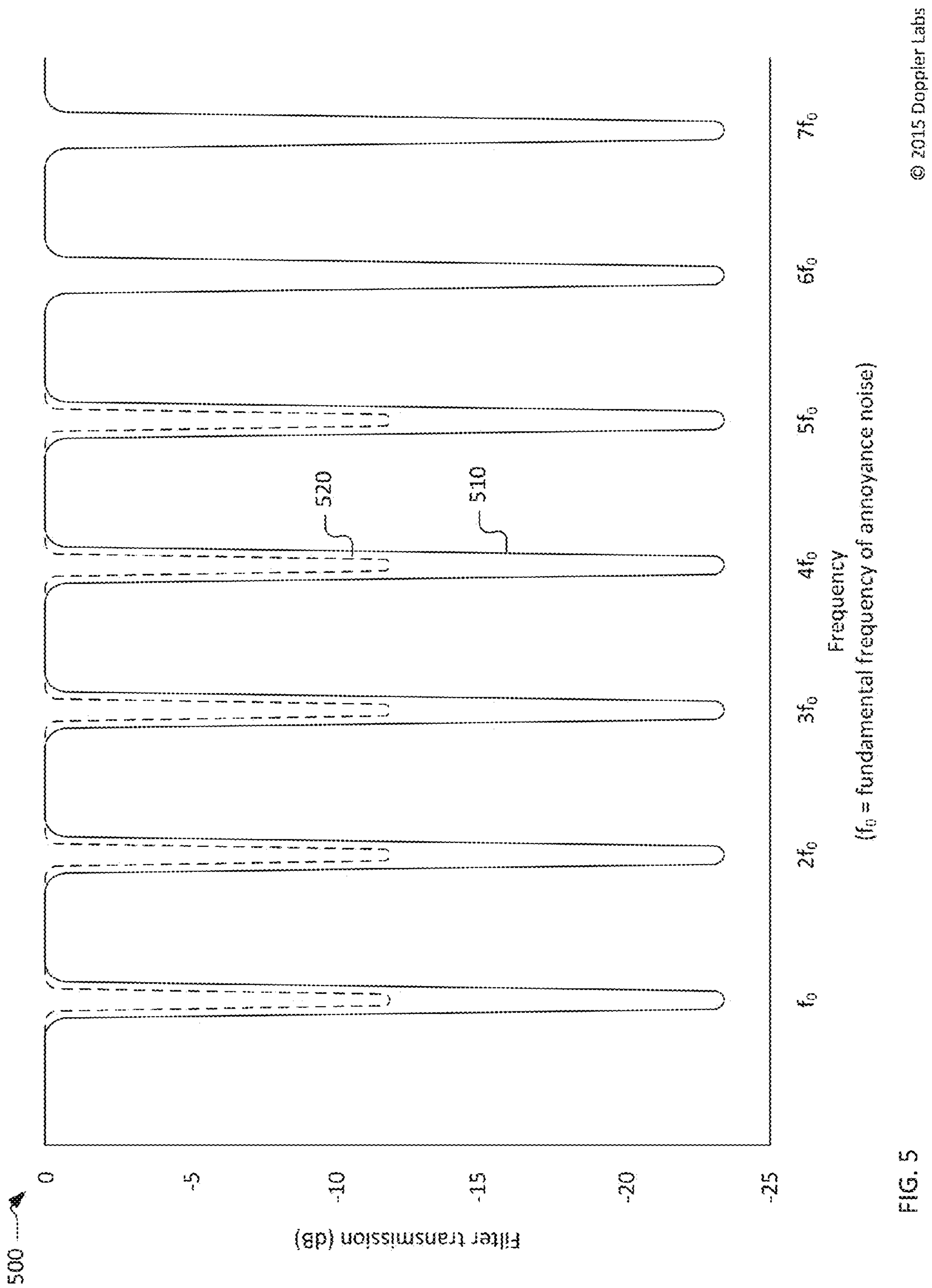
FIG. 5 is a graph showing characteristics of an annoyance noise suppression filter and a compromise noise/voice filter.

FIG. 5 shows a graph 500 showing the throughput of an exemplary processor, which may be the processor 410. When voice activity is not detected, the exemplary processor implements a first filter function, indicated by the solid line 510, intended to substantially suppress the annoyance noise. In this example, the first filter function includes a first bank of seven band reject filters providing about 24 dB attenuation at the fundamental frequency $f_0$ and first six harmonics ($2f_0$ through $7f_0$) of an annoyance noise. The choice of 24 dB attenuation, the illustrated filter bandwidth, and six harmonics are exemplary and a tracking noise suppression filter may provide more or less attenuation and/or more or less filter bandwidth for greater or fewer harmonics. When voice activity is detected (i.e. when both an annoyance noise and speech are present in the digital ambient audio), the exemplary processor implements a second filter function, indicated by the dashed line 520, that is a compromise between annoyance noise suppression and speaker/speech recognition. In this example, the second filter function includes a second bank of band reject filters with lower attenuation and narrower bandwidth at the fundamental frequency and first four harmonics of the annoyance noise. The characteristics of the first and second filter functions are the same at the fifth and sixth harmonic (where the solid line 510 and dashed line 520 are superimposed).

The difference between the first and second filter functions in the graph 500 is also exemplary. In general, a processor may implement a first filter function when voice activity is not detected and a second filter function when both an annoyance noise and voice activity are present in the digital audio stream. The second filter function may provide less attenuation (in the form of lower peak attenuation, narrower bandwidth, or both) than the first filter function for the fundamental component of the annoyance noise. The second filter function may also provide less attenuation than the first filter function for one or more harmonic components of the annoyance noise. The second filter function may provide less attenuation than the first filter function for a predetermined number of harmonic components. In the example of FIG. 5, the second filter function provides less attenuation than the first filter function for the fundamental frequency and the first four lowest-order harmonic components of the fundamental frequency of the annoyance noise. The second filter function may provide less attenuation than the first filter function for harmonic components having frequencies less than a predetermined frequency value. For example, since the human ear is most sensitive to sound frequencies from 2 kHz to 5 kHz, the second filter function may provide less attenuation than the first filter function for harmonic components having frequencies less 2 kHz.

Referring back to FIG. 4, the computational resources and latency time required for the processor 410 to estimate the fundamental frequency and start filtering the annoyance noise may be reduced if parameters of the annoyance noise are known. To this end, the personal audio system 400 may include a class table 450 that lists a plurality of known classes of annoyance noises and corresponding parameters. Techniques for identifying a class of an annoyance noise will be discussed subsequently. Once the annoyance noise class is identified, parameters of the annoyance noise may be retrieved from the corresponding entry in the class table 450.

For example, a parameter that may be retrieved from the class table 450 and provided to the pitch estimator 415 is a fundamental frequency range 452 of the annoyance noise class. Knowing the fundamental frequency range 452 of the annoyance noise class may greatly simplify the problem of identifying and tracking the fundamental frequency of a particular annoyance noise within that class. For example, the pitch estimator 415 may be constrained to find the fundamental frequency within the fundamental frequency range 452 retrieved from the class table 450. Other information that may be retrieved from the class table 450 and provided to the pitch estimator 415 may include an anticipated frequency modulation scheme or a maximum expected rate of change of the fundamental frequency for the identified annoyance noise class. Further, one or more filter parameters 454 may be retrieved from the class table 450 and provided to the filter bank 420. Examples of filter parameters that may be retrieved from the class table 450 for a particular annoyance noise class include a number of harmonics to be filtered, a specified Q (quality factor) of one or more filters, a specified bandwidth of one or more filters, a number of harmonics to be filtered differently by the first and second filter functions implemented by the filer bank 420, expected relative amplitudes of harmonics, and other parameters. The filter parameters 454 may be used to tailor the characteristics of the filter bank 420 to the identified annoyance noise class.

Figure 6A:
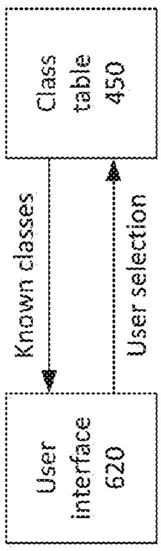
FIG. 6A, FIG. 6B, and FIG. 6C are functional block diagrams of systems for identifying a class of an annoyance noise source.

A number of different systems and associated methods may be used to identify a class of an annoyance noise. The annoyance class may be manually selected by the user of a personal audio system. As shown in FIG. 6A, the class table 450 from the personal audio system 400 may include a name or other identifier (e.g. siren, baby crying, airplane flight, etc.) associated with each known annoyance noise class. The names may be presented to the user via a user interface 620, which may be a user interface of a personal computing device. The user may select one of the names using, for example, a touch screen portion of the user interface. Characteristics of the selected annoyance noise class may then be retrieved from the class table 450.

Figure 6B:
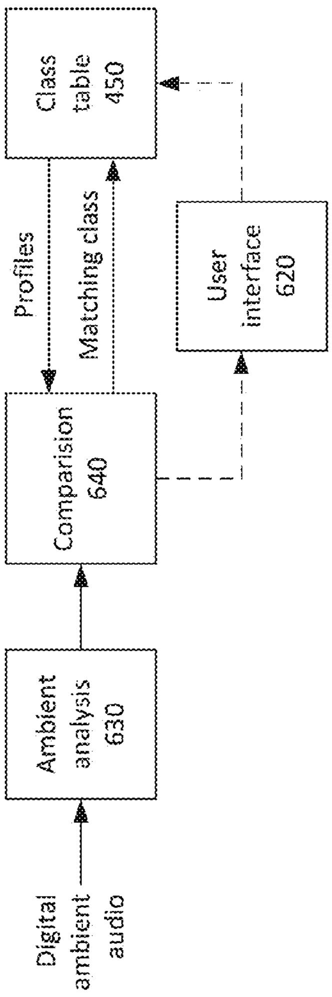

The annoyance class may be selected automatically based on analysis of the digital ambient audio. In this context, "automatically" means without user intervention. As shown in FIG. 6B, the class table 450 from the personal audio system 400 may include a profile of each known annoyance noise class. Each stored annoyance noise class profile may include characteristics such as, for example, an overall loudness level, the normalized or absolute loudness of predetermined frequency bands, the spectral envelop shape, spectrographic features such as rising or falling pitch, the presence and normalized or absolute loudness of dominant narrow-band sounds, the presence or absence of odd and/or even harmonics, the presence and normalized or absolute loudness of noise, low frequency periodicity, and other characteristics. An ambient sound analysis function 630 may develop a corresponding ambient sound profile from the digital ambient audio stream. A comparison function 640 may compare the ambient sound profile from 630 with each of the known annoyance class profiles from the class table 450. The known annoyance class profile that best matches the ambient sound profile may be identified. Characteristics of the corresponding annoyance noise class may then be automatically, meaning without human intervention, retrieved from the class table 450 to be used by the tracking noise suppression filter 410. Optionally, as indicated by the dashed lines, the annoyance noise class automatically identified at 640 may be presented on the user interface 620 for user approval before the characteristics of the corresponding annoyance noise class are retrieved and used to configure the tracking noise suppression filter.

Figure 6C:
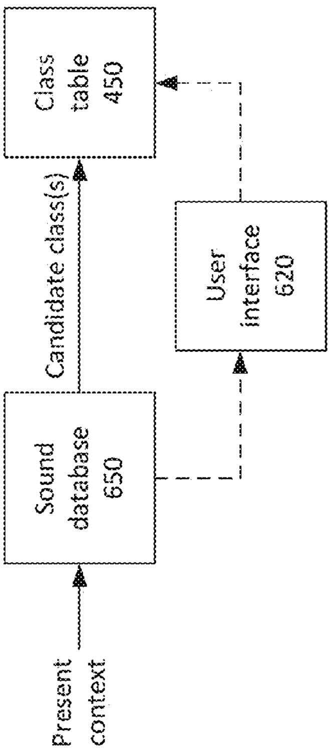

The annoyance noise class may be identified based, at least in part, on a context of the user. As shown in FIG. 6C, a sound database 650 may store data indicating typical or likely sounds as a function of context, where "context" may include parameters such as physical location, user activity, date, and/or time of day. For example, for a user located proximate to a fire station or hospital, a likely or frequent annoyance noise may be "siren". For a user located near the end of an airport runway, the most likely annoyance noise class may be "jet engine" during the operating hours of the airport, but "siren" during times when the airport is closed. In an urban area, the prevalent annoyance noise may be "traffic".

The sound database 650 may be stored in memory within the personal computing device. The sound database 650 may be located within the cloud 130 and accessed via a wireless connection between the personal computing device and the cloud. The sound database 650 may be distributed between the personal computing device and the cloud 130.

A present context of the user may be used to access the sound database 650. For example, data indicating current user location, user activity, date, time, and/or other contextual information may be used to access the sound database 650 to retrieve one or more candidate annoyance noise classes. Characteristics of the corresponding annoyance noise class or classes may then be retrieved from the class table 450. Optionally, as indicated by the dashed lines, the candidate annoyance noise class(es) may be presented on the user interface 620 for user approval before the characteristics of the corresponding annoyance noise class are retrieved from the class table 450 and used to configure the tracking noise suppression filter 410.

The systems shown in FIG. 6A, FIG. 6B, and FIG. 6C and the associated methods are not mutually exclusive. One or more of these techniques and other techniques may be used sequentially or concurrently to identify the class of an annoyance noise.

Description of Processes

Figure 7:
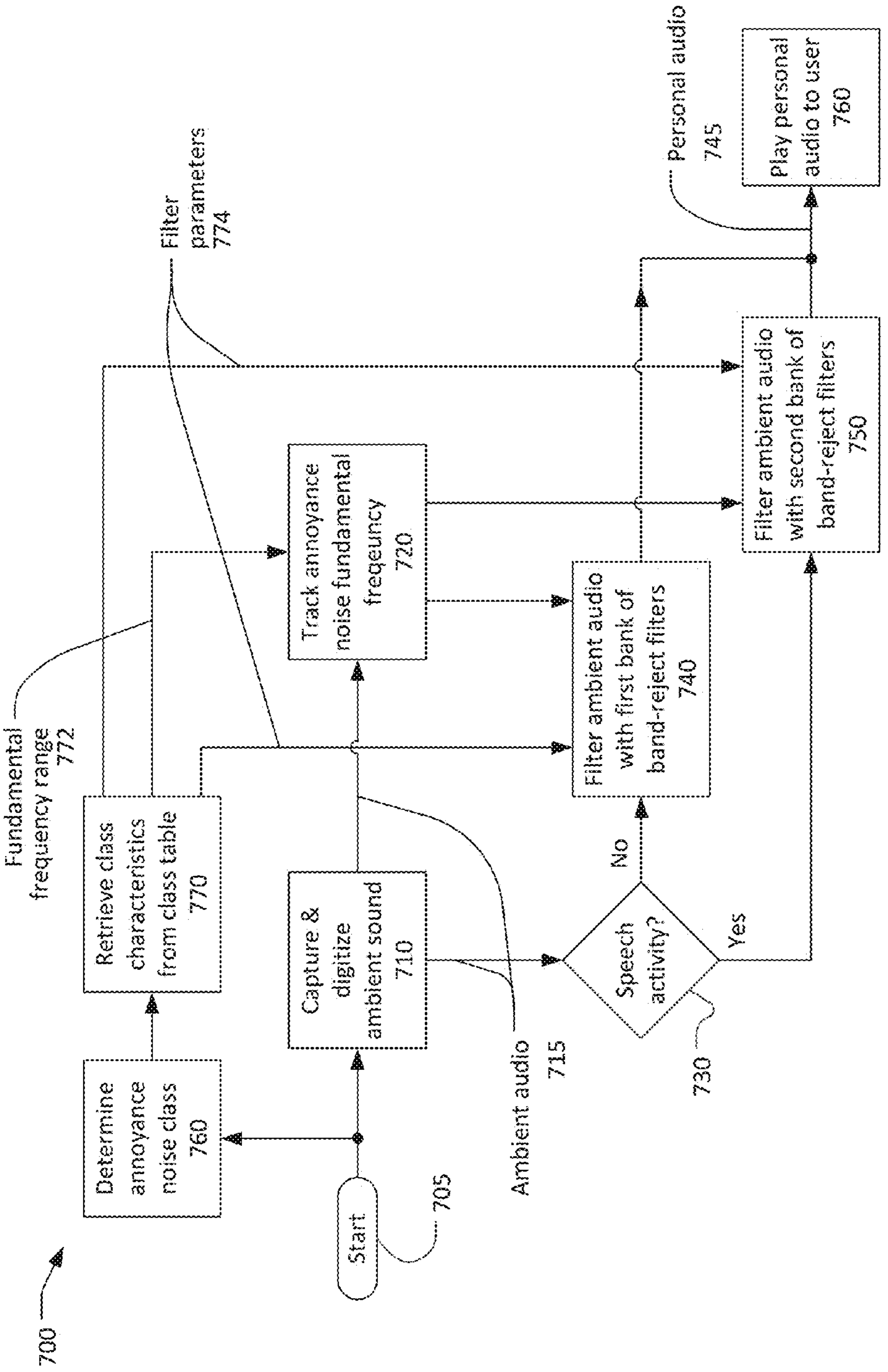
FIG. 7 is a flow chart of a method for suppressing an annoyance noise.

Referring now to FIG. 7, a method 700 for suppressing an annoyance noise in an audio stream may start at 705 and proceed continuously until stopped by a user action (not shown). The method 700 may be performed by a personal audio system, such as the personal audio system 140, which may include one or two active acoustic filters, such as the active acoustic filters 110L, 110R, and a personal computing device, such as the personal computing device 120. All or portions of the method 700 may be performed by hardware, by software running on one or more processors, or by a combination of hardware and software. Although shown as a series of sequential actions for ease of discussion, it must be understood that the actions from 710 to 760 may occur continuously and simultaneously.

At 710 ambient sound may be captured and digitized to provide an ambient audio stream 715. For example, the ambient sound may be converted into an analog signal by the microphone 210, amplified by the preamplifier 215, and digitized by the A/D converter 220 as previously described.

At 720, a fundamental frequency or pitch of an annoyance noise contained in the ambient audio stream 715 may be detected and tracked. Pitch detection or estimation may be performed by time-domain analysis of the ambient audio stream, by frequency-domain analysis of the ambient audio stream, or by a combination of time-domain and frequency-domain techniques. Known pitch detection techniques range from simply measuring the period between zero-crossings of the ambient audio stream in the time domain, to complex frequency-domain analysis such as harmonic product spectrum or cepstral analysis. One or more known, proprietary, or future-developed pitch detection techniques may be used at 720 to estimate and track the fundamental frequency of the ambient audio stream.

At 730, a determination may be made whether or not the ambient audio stream 715 contains speech in addition to an annoyance noise. Voice activity detection is an integral part of many voice-activated systems and applications. Numerous voice activity detection methods are known, as previously described. One or more known voice activity detection techniques or a proprietary technique optimized for detection voice activity in the presence of annoyance noises may be used to make the determination at 730.

When a determination is made at 730 that the ambient audio stream does not contain voice activity ("no" at 730), the ambient audio stream may be filtered at 740 using a first bank of band-reject filters intended to substantially suppress the annoyance noise. The first bank of band-reject filters may include band-reject filters to attenuate a fundamental component (i.e. a component at the fundamental frequency determined at 720) and one or more harmonic components of the annoyance noise.

The personal audio stream 745 output from 740 may be played to a user at 760. For example, the personal audio stream 745 may be converted to an analog signal by the D/A converter 240, amplified by the amplifier 245, and converter to sound waves by the speaker 250 as previously described.

When a determination is made at 730 that the ambient audio stream does contain voice activity ("yes" at 730), the ambient audio stream may be filtered at 750 using a second bank of band-reject filters that is a compromise between annoyance noise suppression and speaker/speech recognition. The second bank of band-reject filters may include band-reject filters to attenuate a fundamental component (i.e. a component at the fundamental frequency determined at 720) and one or more harmonic components of the annoyance noise. The personal audio stream 745 output from the 750 may be played to a user at 760 as previously described.

The filtering performed at 750 using the second bank of band-reject filters may provide less attenuation (in the form of lower peak attenuation, narrower bandwidth, or both) than the filtering performed at 740 using first bank of band-reject filters for the fundamental component of the annoyance noise. The second bank of band-reject filters may also provide less attenuation than the first bank of band-reject filters for one or more harmonic components of the annoyance noise. The second bank of band-reject filters may provide less attenuation than the first bank of band-reject filters for a predetermined number of harmonic components. As shown in the example of FIG. 5, the second bank of band-reject filters provides less attenuation than the first bank of band-reject filters for the fundamental frequency and the first four lowest-order harmonic components of the fundamental frequency of the annoyance noise. The second bank of band-reject filters may provide less attenuation than the first bank of band-reject filters for harmonic components having frequencies less than a predetermined frequency value. For example, since the human ear is most sensitive to sound frequencies from 2 kHz to 5 kHz, the second bank of band-reject filters may provide less attenuation than the first bank of band-reject filters for harmonic components having frequencies less than or equal to 2 kHz.

The computational resources and latency time required to initially estimate the fundamental frequency at 720 and to start filtering the annoyance noise at 740 or 750 may be reduced if one or more characteristics of the annoyance noise are known. To this end, a personal audio system may include a class table that lists known classes of annoyance noises and corresponding characteristics.

An annoyance noise class of the annoyance noise included in the ambient audio stream may be determined at 760. Exemplary methods for determining an annoyance noise class were previously described in conjunction with FIG. 6A, FIG. 6B, and FIG. 6C. Descriptions of these methods will not be repeated. These and other methods for identifying the annoyance noise class may be used at 760.

Characteristics of the annoyance noise class identified at 760 may retrieved from the class table at 770. For example, a fundamental frequency range 772 of the annoyance noise class may be retrieved from the class table at 770 and used to facilitate tracking the annoyance noise fundamental frequency at 720. Knowing the fundamental frequency range 772 of the annoyance noise class may greatly simplify the problem of identifying and tracking the fundamental frequency of a particular annoyance noise. Other information that may be retrieved from the class table at 770 and used to facilitate tracking the annoyance noise fundamental frequency at 720 may include an anticipated frequency modulation scheme or a maximum expected rate of change of the fundamental frequency for the identified annoyance noise class.

Further, one or more filter parameters 774 may be retrieved from the class table 450 and used to configure the first and/or second banks of band-reject filters used at 740 and 750. Filter parameters that may be retrieved from the class table at 770 may include a number of harmonic components to be filtered, a number of harmonics to be filtered differently by the first and second bank of band-reject filters, expected relative amplitudes of harmonic components, and other parameters. Such parameters may be used to tailor the characteristics of the first and/or second banks of band-reject filters used at 740 and 750 for the identified annoyance noise class.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

It is claimed:

1. A personal audio system, comprising:

a voice activity detector to determine whether or not an ambient audio stream contains voice activity; and a processor that processes the ambient audio stream to generate a personal audio stream, the processor comprising:

a pitch estimator to determine a frequency of a fundamental component of an annoyance noise contained in the ambient audio stream and to output a fundamental frequency value of the annoyance noise, wherein the annoyance noise is distinct from ambient noise contained in the ambient audio stream and corresponds to a specific source; and a filter bank including band-reject filters to attenuate the fundamental component and at least one harmonic component of the annoyance noise, wherein the filter bank is configured to:

implement a first filter function when the ambient audio stream does not contain voice activity;

in response to receiving the fundamental frequency value of the annoyance noise from the pitch estimator, adjust the band-reject filters to attenuate the fundamental component and the at least one harmonic component of the annoyance noise; and implement a second filter function, different from the first filter function, when the ambient audio stream contains voice activity and when one or more of the fundamental component and the at least one harmonic component of the annoyance noise overlap with one or more harmonics of a voice associated with the voice activity, wherein the second filter function attenuates the annoyance noise in one or more frequency bands that the annoyance noise overlaps with the voice.

2. The personal audio system of claim 1, wherein the attenuation of the fundamental component of the annoyance noise provided by the first filter function is higher than the attenuation of the fundamental component of the annoyance noise provided by the second filter function.

3. The personal audio system of claim 2, wherein the attenuation of at least one harmonic component of the annoyance noise provided by the first filter function is higher than the attenuation of the corresponding harmonic component of the annoyance noise provided by the second filter function.

4. The personal audio system of claim 2, wherein the attenuation of each of n lowest-order harmonic components of the annoyance noise provided by the first filter function is higher than the attenuation of the corresponding harmonic components of the annoyance noise provided by the second filter function, where n is a positive integer.

5. The personal audio system of claim 4, wherein n=4.

6. The personal audio system of claim 2, wherein the attenuation of each harmonic component of the annoyance noise having a frequency less than a predetermined value provided by the first filter function is higher than the attenuation of the corresponding harmonic components of the annoyance noise provided by the second filter function.

7. The personal audio system of claim 6, wherein the predetermined value is 2 kHz.

8. The personal audio system of claim 1, further comprising:

a class table storing characteristics associated with one or more annoyance noise classes, the class table configured to provide characteristics associated with a selected annoyance class to the processor.

9. The personal audio system of claim 8, wherein the characteristics of the selected annoyance noise class provided to the processor include a fundamental frequency range provided to the pitch estimator.

10. The personal audio system of claim 8, wherein the characteristics of the selected annoyance noise class provided to the processor include a filter parameter provided to the filter bank.

11. The personal audio system of claim 8, further comprising:

a user interface to receive a user input identifying the selected annoyance noise class.

12. The personal audio system of claim 8, wherein the class table stores a profile of each annoyance noise class, and the personal audio system further comprises:

an analyzer to generate a profile of the ambient audio stream; and a comparator to select the annoyance noise class having a stored profile that most closely matches the profile of the ambient audio stream.

13. The personal audio system of claim 8, further comprising:

a sound database that stores user context information and annoyance noise classes, wherein the user context information is associated with the annoyance classes, wherein, the selected annoyance noise class is retrieved from the sound database based on a current context of a user of the personal audio system.

14. The personal audio system of claim 13, wherein the current context of the user includes one or more of date, time, user location, and user activity.

15. A method for suppressing an annoyance noise in an audio stream, comprising:

detecting whether or not an ambient audio stream contains voice activity;

estimating, by a pitch estimator, a frequency of a fundamental component of an annoyance noise contained in the ambient audio stream, wherein the annoyance noise is distinct from ambient noise contained in the ambient audio stream and corresponds to a specific source; and processing the ambient audio stream through a filter bank to generate a personal audio stream, wherein the filter bank includes band-reject filters to attenuate the fundamental component and at least one harmonic component of the annoyance noise, wherein the filter bank is configured to:

implement a first filter function when the ambient audio stream does not contain voice activity;

in response to receiving a fundamental frequency value of the annoyance noise from the pitch estimator, adjust the band-reject filters to attenuate the fundamental component at the least one harmonic component of the annoyance noise; and implement a second filter function, different from the first filter function, when the ambient audio stream contains voice activity and when one or more of the fundamental component and the at least one harmonic component of the annoyance noise overlap with one or more harmonics of a voice associated with the voice activity, wherein the second filter function attenuates the annoyance noise in one or more frequency bands that the annoyance noise overlaps with the voice.

16. The method of claim 15, wherein the attenuation of the fundamental component of the annoyance noise provided by the first filter function is higher than the attenuation of the fundamental component of the annoyance noise provided by the second filter function.

17. The method of claim 16, wherein the attenuation of at least one harmonic component of the annoyance noise provided by the first filter function is higher than the attenuation of the corresponding harmonic component of the annoyance noise provided by the second filter function, where n is a positive integer.

18. The method of claim 16, wherein the attenuation of each of n lowest-order harmonic components of the annoyance noise provided by the first filter function is higher than the corresponding attenuation of each of the n lowest-order harmonic components of the annoyance noise provided by the second filter function, where n is a positive integer.

19. The method of claim 18, wherein n=4.

20. The method of claim 18, wherein the attenuation of each harmonic component of the annoyance noise having a frequency less than a predetermined value provided by the first filter function is higher than the attenuation of the corresponding harmonic components of the annoyance noise provided by the second filter function.

21. The method of claim 20, wherein the predetermined value is 2 kHz.

22. The method of claim 15, further comprising:

storing parameters associated with one or more known annoyance noise classes in a class table; and retrieving parameters of an identified known annoyance class from the class table to assist in suppressing the annoyance noise.

23. The method of claim 22, wherein retrieving parameters of an identified known annoyance class includes retrieving a fundamental frequency range to constrain the frequency of the fundamental component of an annoyance noise.

24. The method of claim 22, wherein retrieving characteristics of an identified known annoyance class includes retrieving a filter parameter to assist in configuring at least one of the first and second band-reject filter banks.

25. The method of claim 22, further comprising:

receiving a user input identifying the selected annoyance noise class.

26. The method of claim 22, wherein the class table stores a profile of each annoyance noise class, and the method further comprises:

generating a profile of the ambient audio stream; and selecting an annoyance noise class having a stored profile that most closely matches the profile of the ambient audio stream.

27. The method of claim 22, further comprising:

retrieving, from a sound database that stores user context information and annoyance noise classes, the selected annoyance noise class based on a current context of a user of the personal audio system, wherein the user context information is associated with the annoyance classes.

28. The method of claim 27, wherein the current context of the user includes one or more of date, time, user location, and user activity.

* * * * *